United States Patent [19]
Hyttinen et al.

[11] Patent Number: 5,959,171
[45] Date of Patent: *Sep. 28, 1999

[54] METHOD FOR THE PRODUCTION OF BIOLOGICALLY ACTIVE POLYPEPTIDES IN A MAMMAL'S MILK AS FUSION PROTEINS THAT ARE LESS ACTIVE THAN THE FREE POLYPEPTIDES, OR NON-ACTIVE

[75] Inventors: Juha-Matti Hyttinen, Kuopio; Veli-Pekka Korhonen, Toivala; Juhani Jänne, Vuorela, all of Finland

[73] Assignee: Pharming B.V., CA Leiden, Netherlands

[*] Notice: This patent is subject to a terminal disclaimer.

[21] Appl. No.: 08/291,074

[22] Filed: Aug. 17, 1994

[51] Int. Cl.⁶ ............................ C12N 5/00; C12N 15/00; C12N 21/06; C12N 21/04
[52] U.S. Cl. ................. 800/2; 800/DIG. 1; 435/69.1; 435/69.7; 435/320.1; 935/60
[58] Field of Search .................. 800/2, DIG. 1; 435/69.1, 69.7, 320.1; 935/60

[56] References Cited
U.S. PATENT DOCUMENTS 4,873,316 10/1989 Meade et al. ........................... 530/412

FOREIGN PATENT DOCUMENTS

WO 91/13151   9/1991   WIPO .

OTHER PUBLICATIONS

Archibald et al (1990) Proced. Natl. Acad. Sci. 87, 5178–5182.

Luthi et al (1992) Eu. J. Biochem. 205, 483–490.

Massoud et al (1996) Reprod. Nutr. Devel. 36, 555–563.

Archer et al (1994) Proc. Nat. Acad. Sci. 91, 6840–6844.

Primary Examiner—Deborah Crouch
Attorney, Agent, or Firm—Townsend & Townsend & Crew

[57] ABSTRACT

A process is disclosed for the production of a protein or polypeptide in the milk of a transgenic non-human mammal where the protein or polypeptide is produced as fusion protein with another protein. The fusion protein can then be cleaved to release the protein or polypeptide. This method would reduce or prevent the formation of side effects associated with ectopic expression or leakage of the protein or polypeptide. Such a fusion protein is β-lactoglobulin-EPO, where biologically active EPO is released upon cleavage of the fusion protein.

9 Claims, 2 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (xi) SEQUENCE DESCRIPTION: SEQ ID NO:1:

TTACCTGTCT TGTGGCTGTT GCT      23

(2) INFORMATION FOR SEQ ID NO:2:

```
        (i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:2:

GTGCAGTGGT GTGATCACAG CT                                                     22

(2) INFORMATION FOR SEQ ID NO:3:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:3:

TTTCGAGTCA TCTGTCCCCT GTCCTG                                                 26

(2) INFORMATION FOR SEQ ID NO:4:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (xi) SEQUENCE DESCRIPTION: SEQ ID NO:4:

TTTCGAACCA AGACCACCTG CCCCACCAGC CCTCATC                                     37

(2) INFORMATION FOR SEQ ID NO:5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:5:

GCCTCCTATT GTCCTCGTAG A                                                      21

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:6:

CGTCACAGCC TCCCTTGGTC                                                        20
```

METHOD FOR THE PRODUCTION OF BIOLOGICALLY ACTIVE POLYPEPTIDES IN A MAMMAL'S MILK AS FUSION PROTEINS THAT ARE LESS ACTIVE THAN THE FREE POLYPEPTIDES, OR NON-ACTIVE

FIELD OF THE INVENTION

The present invention provides a method for the production of biologically active polypeptides in a mammal's milk as fusion proteins that are less active than said biologically active polypeptides in their free form, or non-active.

BACKGROUND OF THE INVENTION

The publications and other materials used herein to illuminate the background of the invention, and in particular, cases to provide additional details respecting the practice, are incorporated by reference.

The general idea of producing valuable proteins into milk using transgene technology was suggested early 1986 (EP 264166, WO 88/00239), but only recently the first true transgenic bioreactors were produced: sheep producing human $\alpha_1$AT, goats secreting human tPA and pigs producing human protein C (Wright G et al., Biotechnology vol 9, Sep 1991; Ebert, Karl M et al., Biotechnology vol 9, Sep 1991; Velander, William H et al., Proc Natl Acad Sci vol 89, 12003–7, Dec 1992). The results from those transgenic farm animals and numerous rodent studies have shown that the mammary gland is able to perform posttranslational modifications like glycosylations (N- and O-glycosylations), gammacarboxylations, sulfhydryl bondings and to secrete large amounts of recombinant proteins constitutively into milk during lactation.

Milk protein genes are under particularly complex regulation. Transcriptional and translational activity of milk protein genes are regulated by interactions between cells, between cells and extracellular matrix and by hormonally induced factors (Harris S et al., J Reprod Fert (1990) 88, 707–715). However, most gene constructs, including intact milk protein genes, designed for mammary gland specific expression in transgenic female mammals have shown not to be completely tissue specific (Archibald Alan L et al., Proc Natl Acad Sci vol 87, 5178–82, July 1990; Reddy V B et al., Animal Biotechnology, 2(1), 15–29 (1991); Roberts B et al., Gene, 121 (1992) 255–262; Persuy M-A et al., Eur J Biochem 205, 887–893 (1992)). The reasons for the unspecific expression are related to the gene constructs, the recombinant genes may not contain all the necessary regulatory elements needed for high level, mammary gland-specific expression or the clonings may have created novel tissue specificities (Günzburg, Walter H et al., Mol Endo 1991, 123–133). Surprisingly Grusby (Grusby M J et al., Proc Natl Acad Sci vol 87, 6897–6901, Sep 1990) found $\alpha$-, $\beta$- and kappa-casein transcripts in mouse cytotoxic T lymphocytes and Maschio (Maschio A et al., Biochem J (1991) 275, 459–467) reported milk protein transcripts in lactating mouse sebaceous glands suggesting that milk protein genes may not be exclusively mammary gland specific.

Milk whey proteins, $\alpha$-lactalbumin and $\beta$-lactoglobulin, have been found in the serum of dairy cattle. The concentrations were at highest at parturition (0.5–1 mg/l) and stabilized later at levels of 20–150 ng/l (Mao, Franc C et al., J Dairy Sci 74:2952–58 (1991)). Rabbit whey acidic protein have been found also in serum during lactation (Grabowski H et al., J Dairy Sci 74: 4143–4150 (1991)). It is possible that overaccumulation of milk between milkings is partly compensated by the release of milk protein including the transgene product into blood through a leaky mammary epithelium (Stinnakre M-G et al., Animal Biotechnology, 3(2), 245–255 (1992). Carver (Carver A et al., Cytotechnology 9: 77–84, 1992) found by studying the human $\alpha_1$AT producing sheep that the transgene product was found in serum of males and females and blood human $\alpha_1$AT concentrations increased upto the range of milligrams per liter to grams per liter during the lactations. Transgenic rats expressing human growth hormone in their milk secreted hGH also into their serum and they exihibited some side effects associated with the elevated hGH concentrations (Ninomiya T et al., Molecular Reproduction and Development 37:276–283 (1994)). The inventors of the present invention have also, as will be reported below, observed elevated human erythropoietin concentrations in the serum of transgenic mice designed to produce human erythropoietin in their milk.

To offer a practically applicable alternative to mammalian tissue culture systems it is important that the producer animals remain healthy also during lactation. Human $\alpha_1$AT, tPA and protein C are quite harmless as they are found normally in high quantities in production animals. Apparently the production animals of these proteins have remained in good condition. Severe side effects are, however, probable when producing potent polypeptides like growth factors, cytokines or enzymes, if the gene construct is expressed unspecifically in other tissues than mammary gland or if there is a leakage of the product from the milk into the blood serum. Even low serum levels (less than 1 ng/ml) of a potent polypeptide may be sufficient to cause health problems, especially when the secretion during lactations is more or less constitutive.

The production of desired polypeptides as biologically less active or inactive fusion proteins into the milk of mammals to minimize health problems and possible aglaction has not been reported before the date of the present invention.

SUMMARY OF THE INVENTION

The present invention relates to a method for the production of biologically active polypeptides in a mammal's milk as fusion proteins that are less active than said biologically active polypeptide in its free form, or non-active. The activity is diminished or removed by having the biologically active polypeptides produced as fusion proteins. By producing the desired polypeptides as fusion proteins the adverse effects caused by possible ectopic expression and/or leakage of the product from milk into the general circulation are minimized or completely avoided and the producing animals remain healthy.

One object of the present invention is to provide a process for the production and secretion of a biologically active polypeptide as a fusion protein into the milk of a mammal without causing to said mammal severe side effects associated with ectopic expression or leakage of said polypeptide.

Another object of the invention is to provide a fusion protein, which is less active than the biologically active polypeptide in free form or non-active, which fusion protein comprises the biologically active polypeptide linked to a milk-specific polypeptide or a non-milk polypeptide, via a peptide or amino acid that can be cleaved to release the desired biologically active polypeptide in its free native form.

A further object of the invention is to provide an expression system for the production of a fusion protein.

Still a further object of the invention is to provide a transgenic mammal or a mammal with transgenic mammary tissue comprising said expression system.

DETAILED DESCRIPTION OF THE INVENTION

Figure 1:
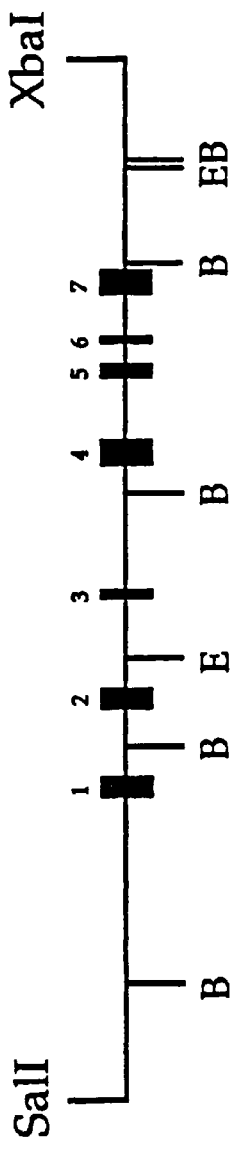
FIG. 1 represents the structure of the bovine β-lactoglobulin clone βLG39SX (9.5 kb) and the βLGEPO (10.0 kb). B=BamHI, E=EcoRI.
Figure 1:
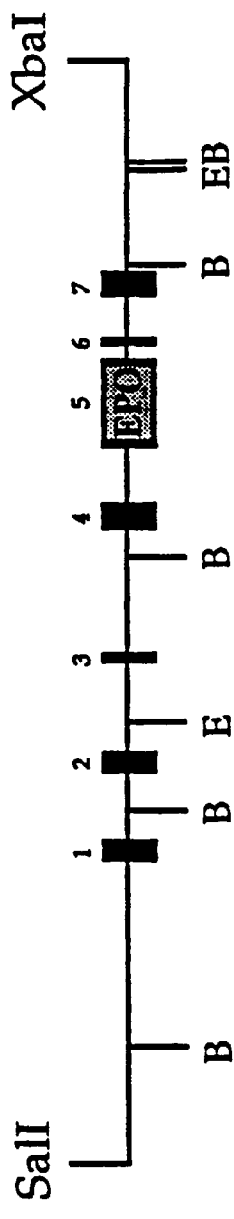

The invention relates to a process for the production and secretion of a biologically active polypeptide into the milk of a mammal without causing to said mammal severe side effects associated with ectopic expression or leakage of said polypeptide by reducing the biological activity of the desired polypeptide by fusing it to another polypeptide, said process comprising the steps of a) creating a mammary gland specific expression system comprising
  1) regulatory elements needed for high level mammary gland specific expression derived from a milk protein gene or a mammary tumor virus,
  2) a DNA sequence encoding signal sequence needed for secretion and maturation of the fusion protein,
  3) a recombinant DNA encoding a fragment or intact milk or non-milk protein,
  4) optionally a linker DNA sequence, and
  5) a recombinant DNA encoding said biologically active polypeptide,
  said expression system being able to produce said biologically active polypeptide fused to said fragment or intact milk or non-milk protein,
b) producing either
  i) a transgenic mammal by introducing said expression system from step a) into a developing mammalian zygote or embryo, or
  ii) a transgenic mammary tissue of a mammal by introducing said expression system from step a) wherein said mammal secretes into milk a fusion protein comprising said biologically active polypeptide fused to said fragment or intact milk or non-milk protein,
c) collecting the milk,
d) isolating said recombinant fusion protein from the milk,
e) cleaving said fusion protein to release said biologically active polypeptide from said fusion protein, and
f) purifying said biologically active polypeptide.

The invention concerns further the novel expression system as defined in step a) above.

The invention concerns further the novel transgenic mammal derived in step b) i) and the novel mammal with transgenic mammary tissue derived in step b) ii) where said mammal is selected from a group consisting of mouse, rat, rabbit, sheep, pig and cattle.

Furthermore, the invention concerns the novel fusion protein produced in step b), said fusion protein having a formula selected from the group consisting of R1-L-R2, R2L-R1, R1-L-R3 and R3-L-R1, wherein R1 represents the desired biologically active polypeptide, R2 is a milk specific polypeptide, R3 is a non-milk polypeptide and L is a peptide or an amino acid suitable for enzymatic or chemical cleavage of said fusion protein.

The biologically active polypeptide shall be understood to cover any potent polypeptide that in its free form could cause adverse effects in the producing mammal. Such polypeptides are for example growth factors, cytokines, enzymes and the like. The biologically active polypeptide includes also more harmless polypeptides which could be produced according to this invention e.g. in order to make the purification easier.

The expression system can generally be described as follows:

Generally speaking the expression system comprises mammary gland specific regulatory elements operatively linked to a DNA encoding for the fusion protein through a DNA sequence encoding for a signal peptide. The expression system is highly active in mammary tissue during lactation producing high levels of fusion protein into mammal's milk.

The regulatory elements are actually clusters of binding sites of different polypeptides regulating transcription. Typical regulatory elements are promoters (determine quantity, accuracy of initiation and polarity of transcription), enhancers (specify the rate of transcription with the promoter), silencers (specify the rate of transcription with the promoter) and polyadenylation signals. Preferably the regulatory elements contain in addition to promoters, enhancers, silencers and polyadenylation signals also so called dominant control regions (DCR, specify overall on-off state of a gene), which make possible position independent and copy number dependent expression. The regulatory elements may be derived from a milk protein gene or mammary tumor virus. Of course regulatory elements from several milk protein genes/viruses may be combined when making the expression system. Useful milk protein genes are for example alpha-, beta- and kappa-casein, beta-lactoglobulin, alpha-lactalbumin and whey acidic protein encoding genes. Among the useful mammary specific viruses where regulatory sequences may be derived can be mentioned mouse mammary tumor virus (MMTV). The regulatory elements may be located in the 5' and 3' flanking sequences and in the structural portion of the milk protein genes and in the long terminal repeat of MMTV.

The signal peptide in the expression system permits the maturation of the fusion protein in the mammary tissue and secretion into milk. The size and origin of the signal peptide in the expression system is not critical as long as the signal peptide enables maturation and secretion of the fusion protein. Preferably the DNA encoding for the signal peptide is derived from the same milk protein gene as the regulatory sequences.

The recombinant DNA encoding a fragment or intact milk or non-milk protein provides the other part to the fusion protein. This polypeptide is used to reduce the biological activity of the desired polypeptide. In addition to reducing the biological activity, the polypeptide may be used to facilitate purification and/or identification of the fusion protein. The recombinant DNA is derived either from a cDNA or a structural gene or from both (so called minigene).

The linker DNA sequence between the DNAs encoding the N- and C-terminal parts of the fusion protein encodes a peptide or an aminoacid which enables the cleavage of the fusion protein either chemically or enzymatically. By choosing a suitable linker DNA sequence, for example encoding the cleavage site of enterokinase, factor Xa or IgA protease to each application, it is possible to release the desired polypeptide from the fusion protein in biologically active and intact form (no aminoacid changes). The linker DNA is cloned in the same reading frame as the N- and C-terminal parts of the fusion protein. The linker DNA sequence is unnecessary when the proteins being fused contain amino- or carboxy-terminal regions which can be used to cleave the fusion protein chemically or enzymatically.

The recombinant DNA encoding the biologically active polypeptide is cloned, in the same reading frame, either 5' or 3' to the recombinant DNA sequence encoding the other polypeptide used to reduce the biological activity of the desired polypeptide. The recombinant DNA is derived either from a cDNA or a structural gene or from both (minigene).

The desired expression system comprises, in its simplest form, a milk protein gene (expressed efficiently in the mammary tissue) into which a recombinant DNA encoding the desired biologically active polypeptide is inserted in such a way that the expression system produces a fusion protein where the signal peptide and the N-terminal part are derived from the milk protein and the polypeptides are separated by a linker. More complicated expression systems are readily made using standard recombinant techniques by anyone skilled in the art.

One technique to produce transgenic whole animals is to microinject the DNA containing the expression system into the pronuclei of the fertilized eggs. One technique to produce genetically engineered mammary tissues (and other mammalian tissues) would be to infuse a DNA solution into virgin mammary glands and induce lactation hormonally (U.S. Pat. No. 5,215,904 (Gould et al.) and GB 2 223 755 (Evans)). Transgenic animals have the advantage compared to mammals having only transgenic tissues that they usually transmit the expression system through the germ line to the next generation. On the other hand mammals having only transgenic mammary tissues would be much faster to produce than whole transgenic farm animals. Preferably the mammals used to produce fusion proteins produce large amounts of milk and have long lactation periods like rabbits, sheep, goats and cattle.

In the formulas for the produced fusion protein, namely R1-L-R2 or R2-L-R1 and R1-L-R3 or R3-L-R1 the desired biologically active polypeptide R1 is linked via the peptide or amino acid L either to the N-terminal amino acid residue or to the C-terminal amino acid residue of the polypeptide R2 or R3, respectively. As examples of R2 can be mentioned alpha-, beta- or kappa-casein, alpha-lactalbumin, beta-lactoglobulin or whey acidic protein, or a fragment thereof. The link L is preferably a peptide or an amino acid for chemical cleavage e.g. with cyanogen bromide or for enzymatic cleavage with an endoprotease such as enterokinase, factor Xa, thrombin, IgA protease or chymosin. Preferably the linker sequence is not cleaved in plasma or in the mammary gland.

According to a preferred embodiment, a milk protein gene which is expressed efficiently in transgenic mammals, is used as a mammary gland specific vector and the desired polypeptide coding sequence (cDNA or genomic fragment) is cloned inside (in the same reading frame) of the coding sequence of the milk protein gene. A linker sequence is added between the milk protein gene and the desired polypeptide coding sequence to make it possible to chemically or enzymatically cleave the produced fusion protein to release the desired polypeptide in biologically active form.

The gene construct is used to produce transgenic mammals or mammary tissues and the desired polypeptide is harvested as a fusion protein from milk of transgenic female mammals. The desired polypeptide is cleaved off from the fusion protein and further purified.

The invention enables the production of high quantities of biologically active polypeptides such as enzymes, growth factors and the like, into the milk of mammals with less side effects to the producer animal. The invention thus broadens the spectrum of compounds that can be produced in the milk of mammals. Also quite harmless proteins may be produced according to this invention e.g. to make the purification easier.

The invention will be illuminated by the following non-restrictive examples. In the examples, Example 1 is a reference example illustrating the production of a potent polypeptide (human erythropoietin or hEPO) directly in its active form in transgenic mice according to known technology. The remining examples present the production of the same polypeptide as a non-active or less active fusion protein according to the present invention. To diminish the activity of hEPO the cDNA fragment coding for mature hEPO was fused into the fifth exon of the bovine β-lactoglobulin gene. The resulting protein contained the aminoacids 1 to 136 of bovine β-lactoglobulin, IgA restriction protease cleavage site and human erythropoietin. IgA protease was chosen because of its nonmammamilian origin. As demonstrated by Examples 2 and 3 below, the bovine β-lactoglobulin regulatory sequences directed the expression of the β-lactoglobulin—human erythropoietin gene into the mammary glands of transgenic mice.

EXAMPLE 1

Production of erythropoietin in its active form in transgenic mice.

Human erythropoietin, which is normally present in human serum at a level of 4 to 90 pg/ml, was produced in transgenic mouse milk. The AHRECASEPO gene construct (Hyttinen et al., Bio/Technology Vol. 12 June 1994 p. 606–608) was designed to secrete biologically active free human erythropoietin into milk. Genomic sequences encoding mature human erythropoietin were regulated by bovine αS1-casein promoter and polyadenylation sequences and chicken A element—mouse mammary tumor virus hormone response element sequences 5' to casein promoter.

The plasmid pAHRECASEPO coding for human erythropoietin was propagated in $E.Coli$ strain TG-1 and plasmid DNA was prepared using Magic Minipreps (Promega, USA) purification system. The AHRECASEPO insert was cut off using NotI and SalI and the insert DNA was purified from Seaplaque agarose (FMC, USA) using phenol and LiCl (Favre D, BioTechniques Vol. 13, No. 1 (1992), pp. 22–26). After two sequential precipitations and washes the AHRECASEPO DNA was dissolved into 2 mM Tris, 0.13 mM EDTA pH 7.5-buffer and gel filtrated through a Nick column (Pharmacia, Sweden). The purified AHRECASEPO DNA was diluted to 2 $\mu$g/ml and sterilized by filtrating through Millex CV4 filter (Millipore, USA).

Transgenic mice were produced using standard technique (Hogan et al., Manipulating the Mouse Embryo, A Laboratory Manual, Cold Spring Harbor Laboratory, Cold Spring N.Y. pp. 1–322 (1986)). Zygotes for microinjections were obtained from superovulated CD2F1 female mice mated with CD2F1 males. After microinjections the zygotes were transferred at one or two cell stage into the oviducts of pseudopregnant foster mothers (CD2F1 mice).

The tail biopsies of the G0 mice were screened with AHRECASEPO transgene specific primers using modified PCR-protocol of Whitelaw et al., Transgenic Research, 1, 3–13 (1991). Tail samples were lysed into 0.5 ml sample buffer (10 mM Tris-HCl pH 8.0, 1 mM EDTA, 0.3M NaAc, 1% SDS, 200 $\mu$g/ml proteinase K) for 3 h, +60° C., chilled on ice for 1 h and centrifuged 14000×g, +4° C. for 10 min.

Light paraffin oil (50 μl) and samples (0.5 μl) were pipetted into 0.5 ml tubes before heating the samples to 90° C. and adding 50 μl of reaction mixture containing 10 mM Tris-HCl pH 8.9, 2.0 mM MgCl$_2$, 50 mM KCl, 20 pmol of primers 695 (5'-TTACCTGTCTTGTGGCTGTTGCT-3') and 220 (5'-GTGCAGTGGTGTGATCACAGCT-3'), 0.2 mM dNTPs, 0.1% Triton X-100 and 1.5 U Taq DNA polymerase (Promega, USA). After 32 cycles of amplification (30 s +95° C., 30 s +60° C., 90 s +72° C.), 10 μl aliquots of each reaction mixture were removed, electrophoresed 150 V for 45 min (1.5% SeaKem GTG agarose (FMC, USA)), stained with ethidium bromide and documented under ultraviolet light.

The transgenic mice were mated and female G0 and G1 animals were milked 10 d after partition. Milk samples (100–600 μl) were collected from anesthetized mice injected with 0.5 U oxitocin, divided into aliquots and frozen to −70° C.

Before milking blood samples (9 μl) were taken from the orbital sinus and the hematocrits were measured using Ames Microspin centrifuge (Bayer Diagnostic GmbH, Germany) according to manufacturers instruction. Some of the milked mice were sacrified and tissue samples and serum were prepared and frozen, −70° C.

The concentrations of hEPO in the milk and serum of the various mouse lines were measured using ELISA assay (Boehringer Mannheim, Germany). The results are shown in Table 1 below. As can be seen from Table 1, although the hEPO levels are rather low (ranging from 2 to 190 ng/ml) and the serum hEPO levels are even lower (0.1 to 2 ng/ml) the side effect (high hematocrits) are evident. As a result of the strongly elevated hematocrit values (0.75 to 0.85 (%/100)) some of the mice suffered from severe polycytemia and their lifespan were only 3 to 8 months. Using reverse transcriptase—polymerase chain reaction assay (Kawasaki ES and Wang AM, Detection of gene expression, PCR Technology, edited by HA Erlich, Chapter 8 pp. 89–97) low levels of transgene specific mRNA could be detected in mammary gland specific total RNA in different transgenic mice lines.

TABLE 1

| Mouse line | hEPO in milk (ng/ml) | hEpo in serum (ng/ml) | B-HKR (%/100) |
| --- | --- | --- | --- |
| UKU49 | 20 | N.D. | 0.78 |
| UKU51 | 187 | 0.087 | 0.85 |
| UKU52 | 6.6 | 2.0 | 0.72 |
| UKU53 | <2.5 | N.D. | 0.48 |
| UKU55 | 90 | 0.92 | 0.85 |
| UKU57 | 10 | 0.75 | 0.75 |
| UKU59 | 62 | 1.5 | 0.85 |

EXAMPLE 2

Preparation of the fusion gene construct

Genomic clone of bovine β-lactoglobulin was isolated from bovine genomic library (bull sperm genomic library (lambda-GEM11), Promega, USA) following manufacturers instructions. Single stranded probe specific for bovine β-lactoglobulin was prepared and labelled ($^{32}$P-dCTP) with polymerase chain reaction (PCR) (Konat et al., Technique—A Journal of Methods in Cell and Molecular Biology, vol 3, no 2, 64–68, 1991). The probe corresponded to bases 2027–2297 of published bovine β-lactoglobulin sequence complementary strand (Alexander at al., Animal Biotechnology, 4(1), 1–10, 1993). Eight lambda-clones were isolated and from clone lambda-βLG39 SalI-XbaI fragment was subcloned into PNEB 193 (New England Biolabs, USA). The plasmid pβLG39SX containing β-lactoglobulin transcription unit (4.7 kb) with 2.8 kb 5' and 1.9 kb 3' flanking sequences was sequenced using automated fluorescent sequencer, A.L.F. (Pharmacia, Sweden). The pβLG39SX coded the β-variant of the protein and the gene was functional. The isolated SalI-XbaI fragment was expressed specifically in the mammary glands of transgenic mice. Three out of four transgenic mice lines secreted bovine β-lactoglobulin at concentrations of 1–3 g/l into their milk during lactation making the bovine β-lactoglobulin SalI-XbaI fragment suitable vector candidate for hybrid constructs.

Human EPO coding cDNA fragment corresponding to bases 263–763 (Jacobs et al., Nature 313:806–810 (1985)) was cloned from mammary glands of a transgenic mouse expressing hEPO into its milk using RT-PCR. Total RNA was isolated from the mammary glands by the acid guanidium thiocyanate protocol (P Chomzynski and N Sacchi, Analytical Biochemistry 162, 156–159, 1987). Contaminating DNA was removed by DNAse: 100 μg total RNA was incubated (45 min +37° C.) with 10 U RQ1 DNase (Promega, USA) and 100 U RNasin (Promega, USA) in 5 mM Tris-HCl pH 8.3, 3.25 mM MgCl$_2$, 25 mM KCl and 0.05 mg/ml gelatine in a total volume of 150 μl. After extracting once with phenol and twice with chloroform-isoamylalcohol, the RNA was precipitated, washed and dissolved in sterile water containing RNasin (1 U/μl). Before PCR amplification total RNA (2 μg) was reverse transcribed into cDNA (1 h +37° C.) in a reaction mixture containing 1.3 μg random hexa-nucleotides, 1 mM each dNTP, 1 U/μl RNasin and 5 U AMV-reverse transcriptase (Promega, USA) in 50 mM Tris-HCl pH 8.3, 50 mM KCl, 10 mM MgCl$_2$, 10 mM dithiotreitol and 0.5 mM spermidine.

Human EPO cDNA fragment was amplified from the cDNA using Hot start technique (Ehrlich et al., Science, Vol. 252, Jun. 21, 1991, pp. 1643–51): reaction tubes containing the cDNA sample (corresponding to 100 ng total RNA), 25 μmol of primers 760 (5'-TTTCGAGTC ATCTGTCCCCTGTCCTG-3') and 761 (5'TTT CGAACCAAGACCACCTGCCCCACCAGCCCTCATC-3'), 0.4 mM each dNTP, 10 mM Tris-HCl pH 8.9, 1.5 mM MgCl$_2$, 50 mM KCl, 0.1% Triton X-100 and 50 μl paraffin oil were heated to +90° C. before adding 1.25 U Taq DNA polymerase (Promega, USA) in 25 μl of 10 mM Tris-HCl pH 8.9, 1,5 mM MgCl$_2$, 50 mM KCl, 0.1% Triton X-100. The samples were amplified for 40 cycles using 20 s +96° C. denaturation, 20 s +68–58° C. primer annealing and 1 min +72° C. extension, the annealing temperature was lowered (1° C./cycle) from +68 to +58° C. during the first ten cycles. Amplification product bearing TaqI sites at both ends and IgA restriction protease cleavage site 5' to aminoacid 1 of hEPO was blunted with T4 DNA polymerase, purified from agarose using GeneClean (Bio 101, USA) and cloned into SmaI digested pUC18. Nucleotide sequence of isolated hEPO clones was conformed by DNA sequencing (A.L.F.).

To prepare β-lactoglobulin—hEPO fusion gene a BamHI fragment (corresponding to bases 4932–6988, Alexander et al. 1993) from pβLG39SX was cloned into pNEB193 (pβLGBAM). Human EPO was cloned as a TaqI fragment to the TaqI site (inside the fifth exon of bovine β-lactoglobulin) of the pβLGBAM. The nucleotide sequence of the junction between bovine β-lactoglobulin and hEPO was checked by sequencing. Finally the TthI fragment of pβLG39SX was replaced with the TthI fragment containing hEPO to get pβLGEPO.

EXAMPLE 3

Transgenic mice expressing the fusion gene construct

The plasmid pβLGEPO coding for the bovine βLG—human EPO fusion protein was propagated in *E.Coli* strain TG-1 and plasmid DNA was prepared using Magic Minipreps (Promega, USA) purification system. The βLG-EPO insert was cut off using SalI and XbaI and the insert DNA was purified from Seaplaque agarose (FMC, USA) using phenol and LiCl (Favre 1992). After two sequential precipitations and washes the βLG-EPO DNA was dissolved into 2 mM Tris, 0.13 mM EDTA pH 7.5-buffer and gel filtrated through a Nick column (Pharmacia, Sweden). The purified βLG-EPO DNA was diluted to 2 μg/ml and sterilized by filtrating through Millex CV4 filter (Millipore, USA).

Transgenic mice were produced using standard technique (Hogan et al. 1986). Zygotes for microinjections were obtained from superovulated CD2F1 female mice mated with CD2F1 males. After microinjections zygotes were transferred at one or two cell stage into oviducts of pseudopregnant foster mothers (CD2F1 mice).

The tail biopsies of the G0 mice were screened with bovine β-lactoglobulin specific primers using modified PCR-protocol of Whitelaw et al., 1991. Tail samples were lysed into 0.5 ml sample buffer (10 mM Tris-HCl pH 8.0, 1 mM EDTA, 0.3M NaAc, 1% SDS, 200 μg/ml proteinase K) for 3 h +60° C., chilled on ice for 1 h and centrifuged 14000×g +4° C. for 10 min. Light paraffin oil (50 μl) and samples (0.5 μl) were pipetted into 0.5 ml tubes before heating the samples to 90° C. and adding 50 μl of reaction mixture containing 10 mM Tris-HCl pH 8.8, 1.5 mM $MgCl_2$, 50 mM KCl, 20 pmol of primers 732 (5'-GCCTCCTATTGTCCTCGTAGA-3') and 733 (5'-CGTCACAGCCTCCCTTGGTC-3'), 0.2 mM dNTPs, 0.3% Triton x-100 and 1U Dynazyme (Finnzymes, Finland). After 32 cycles of amplification (30 s +95° C., 30 s +60° C., 90 s +72° C.), 10 μl aliquots of each reaction mixture were removed, electrophoresed 150 V for 45 min (1.5% SeaKem GTG agarose (FMC, USA)), stained with ethidium bromide and documented under ultraviolet light. The transgenic mice were mated and female G0 and G1 animals were milked 10 d after partitition. Milk samples (100–600 μl) were collected from anesthetized mice injected with 0.5 U oxitocin, divided into aliquots and frosen to −70° C. Before milking blood samples (2×9 μl) were taken from the orbital sinus and the hematocrits were measured using Ames Microspin centrifuge (Bayer Diagnostic GmbH, Germany) according to manufacturers instruction.

Milk from transgenic founder mice was analysed by western blotting. Milk samples were diluted 1:5 with distilled water and defatted by centrifugation. Skim milk was mixed with reducing SDS-PAGE sample buffer (65 mM Tris-HCl pH 6.8, 2% SDS, 10% glycerol, 4% mercaptoethanol, 0.01% bromophenol blue), boiled 5 min and centrifuged briefly. Samples corresponding to one μl of milk were electrophoresed in a 12% SDS-polyacrylamide mini-gel (Bio-Rad, USA) at constant current 10 mA/gel and electrophoretically transferred in 25 mM Tris, 198 mM glycine, pH 8.3, 20% methanol (100 V, 1 h) onto Immobilon-P PVDF-membrane (Millipore, USA). After transfer the lane containing molecular weight markers (LMW-markers, Pharmacia, USA) was cut off and stained in 0.1% Coomassie brilliant blue R-350, 10% acetic acid, 30% methanol and destained briefly in 5% acetic acid, 90% methanol. The membrane was blocked 30 min in 2% PM-TBS (2% w/v powdered milk, 10 mM Tris-HCl pH 7.4, 150 mM NaCl) and incubated 4 h with mouse monoclonal antibody to hEPO (Genzyme, USA), diluted to 1 μg/ml with PM-TBS. The blot was washed three times with TBS and then incubated 1 h with alkaline phosphatase labelled goat antimouse antibody (Zymed, USA) diluted 1:1000 in PM-TBS. After three washings with TBS the membrane was developed in alkaline phosphatase substrate solution: 100 mM Tris-HCl pH 9.5, 100 mM NaCl, 5 mM $MgCl_2$, 0.165 mg/ml BCIP, 0.33 mg/ml NBT.

Figure 2:
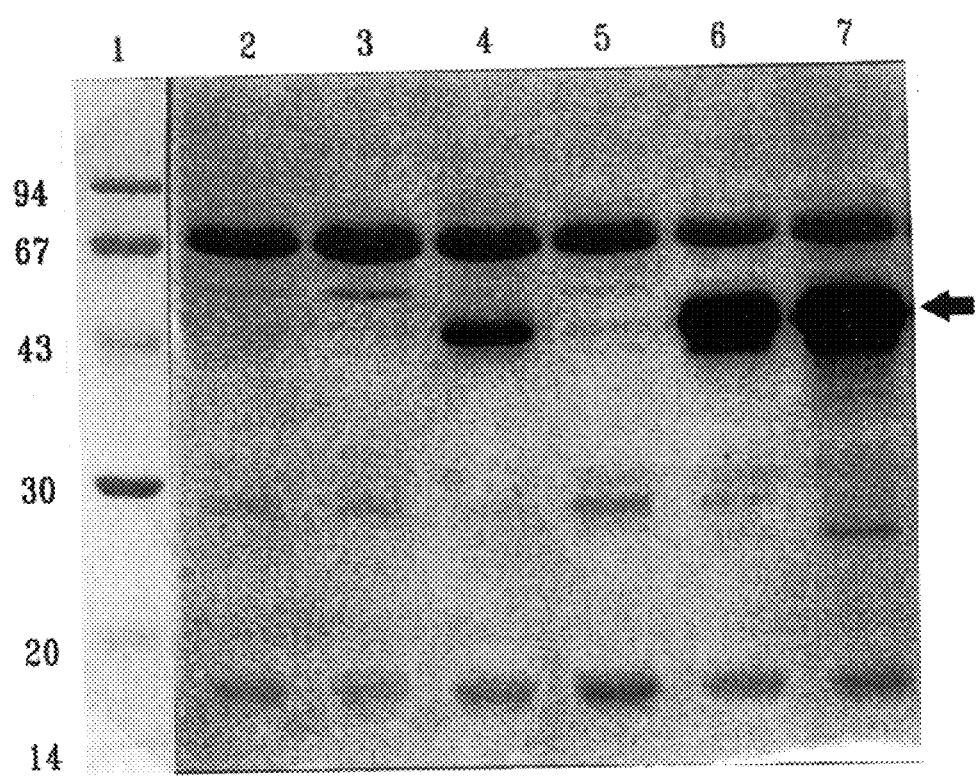
FIG. 2 represents the Western blot analysis of mouse milk samples. Molecular weight markers 14–94 kDa (lane 1), control milk (lane 2), milk from founder 51 expressing AHRECASEPO (lane 3), milk from founder 108 (lane 4), 110 (lane 5), 114 (lane 6) and 115 (lane 7) expressing the βlgEPOfusion protein. The arrow indicates the βlg-EPO fusion protein.

As shown in FIG. 2 three out of four transgenic founder mice produced beta-lactoglobulin-hEPO fusion protein of expected size (about 44 kDa) into milk. The amount of fusion protein in founder mouse 115 was at least 1000 times higher (0.2–1 mg/ml) than hEPO concentration in the milk of mouse line 51 (Example 1). The transgenic mice expressing the fusion protein are so far healthy and the hematocrits were within normal range except in line 115, in which the hematocrit was slightly elevated (0.72).

It will be appreciated that the methods of the present invention can be incorporated in the form of a variety of embodiments, only a few of which are disclosed herein. It will be apparent for the artisan that other embodiments exist and do not depart from the spirit of the invention. Thus, the described embodiments are illustrative and should not be construed as restrictive.

---

We claim:

1. A process for the production of erythropoietin in milk of a transgenic non-human mammal said process comprising the steps of:

a) obtaining a mammary gland specific expression system comprising in operable linkage:

1) expression regulatory elements from a milk protein gene or a mammary tumor virus, 2) a DNA sequence encoding a signal sequence, 3) a DNA sequence encoding a fragment of a non-EPO protein, where the fragment is sufficient to reduce or prevent the formation of side effects associated with ectopic expression or leakage of erythropoietin, or a DNA sequence encoding a non-EPO protein, wherein the protein reduces or prevents the formation of side effects associated with ectopic expression or leakage of erythropoietin, and a 4) a DNA sequence encoding erythropoietin, whereby elements 3) and 4) are linked in frame forming a fusion protein, b) producing a transgenic non-human mammal comprising introducing the expression system of step a) into a non-human mammalian zygote or embryo, and maturing said zygote or embryo into a transgenic non-human mammal, c) expressing said fusion protein such that the fusion protein is secreted into the milk of said mammal, d) collecting said milk from the mammal or a female descendant of said mammal, e) isolating said recombinant fusion protein from said milk, f) releasing erythropoietin from said fusion protein, and g) purifying said erythropoietin.

2. The process of claim 1, further comprising a DNA sequence encoding an enzymatic cleavage site positioned between elements 3) and 4), and where said releasing is by enzymatic cleavage.

3. A mammary gland specific expression system comprising in operable linkage:

a) expression regulatory elements from a milk protein gene or a mammary tumor virus, b) a DNA sequence encoding a signal sequence, c) a DNA sequence encoding a fragment of a non-EPO protein, where the fragment is sufficient to reduce or prevent the formation of side effects associated with ectopic expression or leakage of erythropoietin, or a DNA sequence encoding a non-EPO protein, wherein the protein reduces or prevents the formation of side effects associated with ectopic expression or leakage of erythropoietin, and a d) a DNA sequence encoding erythropoietin, whereby elements 3) and 4) are linked in frame forming a fusion protein.

4. The mammary gland specific expression system of claim 3, further comprising a DNA sequence encoding a cleavage site positioned between elements 3) and 4).

5. The mammary gland specific expression system of claim 4, wherein said cleavage site is for enzymatic cleavage or chemical cleavage.

6. The mammary gland specific expression system of claim 4, wherein said cleavage site is an endoprotease cleavage site.

7. The mammary gland specific expression system of claim 4, wherein said endoprotease is enterokinase, factor Xa, thrombin, IgA protease or chymosin.

8. The mammary gland specific expression system of claim 4, wherein said DNA sequence encoding said fragment of a milk protein, or encoding said a milk protein gene is selected from the group consisting of α-casein, β-casein, κ-casein, α-lactalbumin, β-lactoglobulin and whey acidic protein, and further comprising a DNA sequence encoding an enzymatic cleavage site positioned between elements 3) and 4).

9. A transgenic non-human mammal whose genome comprises the expression system of claim 3, wherein said mammal is selected from the group consisting of mouse, rat, rabbit, sheep, pig and cow, and wherein a detectable level of erythropoietin is expressed in the milk of said transgenic mammal or a descendant of said mammal.

* * * * *